United States Patent [19]

Merger et al.

[11] 4,354,045

[45] Oct. 12, 1982

[54] PREPARATION OF FORMALDEHYDE

[75] Inventors: Franz Merger, Frankenthal; Gerd Fouquet, Neustadt, both of Fed. Rep. of Germany

[73] Assignee: BASF Aktiengesellschaft, Fed. Rep. of Germany

[21] Appl. No.: 221,822

[22] Filed: Dec. 31, 1980

[30] Foreign Application Priority Data

Feb. 7, 1980 [DE] Fed. Rep. of Germany ....... 3004436

[51] Int. Cl.³ ...................... C07C 45/51; C07C 45/65
[52] U.S. Cl. .................................... 568/487; 568/481
[58] Field of Search .............................. 568/487, 481

[56] References Cited

U.S. PATENT DOCUMENTS

| | | | |
|---|---|---|---|
| 2,662,921 | 12/1953 | Middleton | 568/481 |
| 2,669,586 | 2/1954 | Middleton | 568/481 |
| 4,014,939 | 3/1977 | Osugi et al. | 568/487 |
| 4,054,609 | 10/1977 | Osugi et al. | 568/487 |

FOREIGN PATENT DOCUMENTS

| | | | |
|---|---|---|---|
| 495925 | 9/1953 | Canada | 568/487 |
| 728213 | 2/1966 | Canada | 568/481 |
| 1063141 | 8/1959 | Fed. Rep. of Germany | 568/474 |
| 1144252 | 2/1963 | Fed. Rep. of Germany | 568/473 |
| 1162344 | 8/1964 | Fed. Rep. of Germany | 568/473 |
| 1235881 | 3/1967 | Fed. Rep. of Germany | 568/487 |
| 1277834 | 9/1968 | Fed. Rep. of Germany | 568/487 |
| 2525174 | 12/1975 | Fed. Rep. of Germany | 568/487 |
| 2627421 | 1/1977 | Fed. Rep. of Germany | 568/487 |

OTHER PUBLICATIONS

Krylov et al., "Iav. Akad. Nauk SSR Otd Khim Nauk" (1959) pp. 15-20.
Kollonitsch et al., "Hydrocarbon Processing and Petroleum Refining", vol. 43 (1964) No. 6, pp. 139-142.
Fable et al. "Katalysatoren Tenside und Mineralol additive", Thieme Verlag Struttgart, p. 67 (1968).

*Primary Examiner*—Werren B. Lone
*Attorney, Agent, or Firm*—Keil & Witherspoon

[57] ABSTRACT

Formaldehyde is prepared by dehydrogenation of methanol in the presence of a catalyst containing copper, zinc and tellurium, at from 300° to 750° C.

The formaldehyde obtainable by the process of the invention is a disinfectant, tanning agent, reducing agent and valuable starting material for the preparation of synthetic resins, adhesives, plastics and auxiliaries in numerous sectors of industry.

7 Claims, No Drawings

PREPARATION OF FORMALDEHYDE

The invention relates to a process for the preparation of formaldehyde by dehydrogenating methanol in the presence of a catalyst containing copper, zinc and tellurium, at from 300° to 750° C.

German Published Application DAS 1,144,252 and Ullmanns Encyklopädie der technischen Chemie (4th edition), Volume 11, pages 693–696, disclose that methanol can be oxidized to formaldehyde in the presence of a metal oxide catalyst, as a rule over unsupported iron oxide and molybdenum oxide. A similar catalyst which additionally contains cobalt oxide is described in German Pat. No. 1,162,344. German Published Application DAS 1,063,141 describes the oxidation in the presence of similar catalysts, but supported on a carbide and/or iron oxide carrier. Temperatures of 270°–380° C. are specified. All these processes constitute catalytic oxidations which give 37–55 percent strength by weight aqueous formaldehyde solutions. The storage and transportation of such solutions presents difficulties, since paraformaldehyde precipitates are formed and, accordingly, deposits and blockages in the equipment result, unless stabilizers are added or elevated storage temperatures are used. The latter, however, favor the formation of formic acid. The above processes are not used to prepare a solution of formaldehyde in methanol, of low water content.

For the reasons stated above, processes for the preparation of formaldehyde solutions of low water content by using copper/silver/silicon, copper/zinc and zinc/gallium/indium catalysts, aluminum catalysts and zinc catalysts have been developed, and are described in German Laid-Open Application DOS 2,525,174. Dehydrogenation of methanol vapor mixed with hydrogen, at 500°–750° C., using copper, zinc and sulfur as catalyst components, is described as more advantageous than the use of the catalyst metnioned above. German Laid-Open Application DOS 2,627,421 describes a similar process which employs selenium instead of sulfur as a catalyst component. It states that a proportion of the sulfur in the catalyst is, during dehydrogenation, undesirably entrained by the reaction product or by the exit gas. However, it is a disadvantage of the process of German Laid-Open Application DOS 2,627,421 that selenium also is entrained during the reaction and that the catalyst suffers destruction in sustained operation. In particular, it is a disadvantage of both the above processes that sulfur and selenium, especially in the form of hydrogen sulfide and hydrogen selenide contaminate the end product and, when present in the exit gas, cause problems of environmental pollution. The contaminated end product presents difficulties on further processing. Altogether, additional measures, and equipment, become necessary for working up, for purification of the end product and of the exit gas and for regulating and controlling the equipment.

We have found that formaldehyde is obtained in an advantageous manner by dehydrogenating methanol in the presence of a catalyst at an elevated temperature, if the reaction is carried out in the presence of a catalyst containing copper, zinc and tellurium, at from 300° to 750° C.

The reaction can be represented by the following equation:

$$CH_3OH \rightarrow CH_2O + H_2$$

Compared to the conventional processes, the process according to the invention surprisingly gives formaldehyde more simply and more economically, in good yield and high purity. In contrast to the conventional processes which give aqueous formaldehyde solutions, the novel process gives methanolic formaldehyde solutions, advantageously of 10–40 percent strength by weight, which have a low water content, as a rule of less than 1.5 percent by weight, and in most cases of from 0.2 to 0.9 percent by weight, based on the total solution. The catalyst has a substantially longer life and higher activity, the life being, in most cases, 80 operating hours or more, compared to 10 operating hours or less in the case of copper/zinc/sulfur and 40 operating hours or less in the case of copper/zinc/selenium as the catalyst, at similar throughputs. Surprisingly, the addition of hydrogen gas can be dispensed with. In the light of the publications mentioned above, it was not to be expected that hardly any tellurium would be lost from the catalyst during the reaction. For similar reactions, the content of the reaction mixture is as a rule $\leq 0.5$ mg/kg of tellurium in the case of the catalyst according to the invention, from 3 to 175 mg/kg of S in the case of sulfur-containing catalysts and from 3 to 830 mg/kg of Se in the case of selenium-containing catalysts. Accordingly, the process is safer to operate, causes less pollution of the environment and dispenses with additional control and purification operations with special equipment and with frequent catalyst changes. All these advantageous results of the novel process are surprising, especially in view of the fact that J. Falbe and U. Hasserodt, Katalysatoren, Tenside und Mineralöladditive (Thieme Verlag, Stuttgart 1978)explicitly state, on page 67, that catalysts for the oxidation of acrolein to acrylic acid which employ cobalt oxide, molybdenum oxide and tellurium oxide, have not found industrial use specifically because of the volatility of the tellurium.

Pure methanol or technical-grade methanol may be used as a starting material for the process. Crude methanol, which as a rule is purified by treatment with oxidizing agents and/or alkalis, using the processes described in German Published Application DAS 1,277,834 and German Pat. No. 1,235,881, may also be used.

The catalyst advantageously contains the metals in a ratio of one atom of copper to 0.01–0.5, preferably 0.05–0.4, atom of zinc and 0.001–0.3, preferably 0.005–0.2, atom of tellurium. An advantageous ratio is 0.05–0.3 atom of zinc per atom of copper and/or 0.005–0.1 atom of tellurium per atom of copper. In these figures, the elements in the catalyst are referred to, and calculated, as the elements, regardless of the actual constitution. During the reaction, the elements may be present in the catalyst as metals and/or as metal compounds; advantageously, the initial catalyst contains only the metal compounds, and these are partially reduced to the metals in the course of the reaction. It is advantageous to use catalysts which, at the end of the reaction, contain 94.2–66.2 percent by weight of the total copper in the form of metallic copper, 4.9–20.5 percent by weight of the total zinc in the form of metallic zinc and 0.9–13.3 percent by weight of the total tellurium in the form of elementary tellurium.

Suitable compounds of the metals are the hydroxides, oxides, nitrates, bicarbonates, carbonates, acetates and oxalates of copper, zinc and tellurium; oxyacids of tellurium, tellurates such as ammonium tellurate and potassium tellurate, and corresponding tellurites; copper tellurate, zinc tellurate, copper tellurite and zinc tellurite.

Advantageously, the catalyst contains from 10 to 50, preferably from 12 to 40, gram atoms of copper, from 0.5 to 20, preferably from 1 to 15, gram atoms of zinc and from 0.1 to 10, preferably from 0.3 to 8, gram atoms of tellurium per mole of methanol per hour The catalyst is as a rule in the form of particles of any desired shape, but preferably of spherical shape, with diameters of from 2 to 12, preferably of from 3 to 10, millimeters. The catalyst can be prepared in a conventional manner, for example by mixing the copper, zinc and tellurium compounds with a small amount of water and drying the mixture at 100°–140° C. The catalyst can also be dried and activated by heating, for example for from 2 to 4 hours first at from 100° to 140° C. and then at from 140° to 750° C., whereby the compounds are completely or partially converted to the oxides.

The dehydrogenation of the methanol is carried out at from 300° to 750° C., preferably from 320° to 600° C., under atmospheric or superatmospheric pressure, batchwise or, preferably, continuously. The reaction may be effected as follows: a reactor is filled with the catalyst. Preferably, the reactor is a tubular reactor with external cooling and with any appropriate number of tubes, for example with from 8,000 to 15,000 tubes, which are advantageously free from internal fitments, for example heat shafts. In a preferred embodiment, the internal diameter of the tubes is at least 25 millimeters, especially from 25 to 34 millimeters, and the length of the tubes is from 1 to 5 meters. After the reactor has been filled with the catalyst, methanol is passed through it at the above reaction temperature and under the conditions described. As a rule, the methanol is passed through the catalyst bed at a rate of from 0.5 to 10, preferably from 0.8 to 8, kilograms per hour per liter of catalyst. The formaldehyde, or its 15–50 percent strength by weight solution in methanol, is isolated from the reaction mixture, leaving the reactor, in a conventional manner, for example by fractional distillation.

The formaldehyde obtainable by the novel process is a disinfectant, tanning agent, reducing agent and valuable starting material for the manufacture of synthetic resins, adhesives, plastics and auxiliaries for many sectors of industry. Regarding the use of formaldehyde, reference may be made to Ullmanns Encyklopädie der technischen Chemie, Volume 7, page 670.

In the Examples which follow, parts are by weight and bear the same relation to parts by volume of that of the kilogram to the liter. The conversion and selectivity are defined as follows:

$$\text{Conversion } \% = \frac{\text{converted methanol (moles)}}{\text{methanol introduced (moles)}} \times 100$$

$$\text{Selectivity } \% = \frac{\text{formaldehyde formed (moles)}}{\text{methanol converted (moles)}} \times 100$$

EXAMPLE 1

(a) Preparation of the catalyst: 84 parts of copper(II) oxide, 11.8 parts of zinc oxide and 4.2 parts of tellurium dioxide are thoroughly mixed with 50 parts of water and the mixture is dried at 130° C. and converted to pills of 3 mm diameter and 3 mm thickness.

(b) Reaction: 60 parts by volume of the catalyst thus obtained are introduced into a tubular quartz glass reactor ($\phi$ 3.2 cm). 132 parts per hour of methanol are vaporized, passed continuously into the reactor and reacted at 550° C. The reaction mixture is condensed. Per hour, 20.2 parts of formaldehyde (selectivity 76% of theory), 0.5 part of water and 79 parts of methanol are obtained. The conversion is 26 percent and the proportion of entrained tellurium is <0.5 mg/kg of reaction mixture.

EXAMPLE 2

(a) A catalyst is prepared from 74.6 parts of copper(II) oxide, 15 parts of tellurium dioxide and 10.4 parts of zinc oxide, as described in Example 1a.

(b) The reaction, and working-up, are carried out under the conditions described in Example 1. Per hour, 16.4 parts of formaldehyde (selectivity 73% of theory), 0.7 part of water and 83 parts of methanol are obtained. The conversion is 22.6 percent and the proportion of entrained tellurium is <0.5 mg/kg of reaction mixture.

COMPARATIVE EXAMPLE 3

(a) A mixture of 50 parts of copper(II) oxide, 20 parts of ammonium sulfate and 2 parts of zinc oxide is milled. The pulverized mixture is then converted to a paste by adding 30 parts of water and the paste is molded into tablets of 3 mm diameter and 3 mm thickness. The tablets are then reduced in a hydrogen atmosphere for 30 minutes at 200° C. followed by 30 minutes at 600° C.

(b) Using this catalyst, the reaction and working-up are carried out under the same conditions as in Example 1. Per hour, 20.6 parts of formaldehyde (selectivity 67% of theory), 0.6 part of water and 78 parts of methanol are obtained. The conversion is 29 percent and the amount of entrained sulfur is 126 mg/kg of reaction mixture.

COMPARATIVE EXAMPLE 4

(a) Aliquot portions of 50.0 parts of copper(II) oxide, 7.0 parts of selenium dioxide and 7.0 parts of zinc oxide are milled and mixed. 30 parts of water are added to the mixture; a paste is obtained. This is molded into tablets of 3 mm diameter and 3 mm thickness. The tablets thus obtained are reduced for 30 minutes at 650° C. in a stream of hydrogen gas.

(b) Using this catalyst, the reaction and working-up are carried out under the same conditions as in Example 1. Per hour, 19.4 parts of formaldehyde (selectivity 68% of theory), 1.0 part of water and 79 parts of methanol are obtained. The conversion is 27 percent and the amount of entrained selenium is 110 mg/kg of reaction mixture.

EXAMPLE 5

(a) Preparation of the catalyst 85.8 parts of copper(II) oxide, 10 parts of zinc oxide and 4.2 parts of tellurium dioxide are thoroughly mixed with 50 parts of water, and the mixture is dried at 130° C. and converted to pills of 3 mm diameter and 3 mm thickness.

(d) Reaction 60 parts by volume of the catalyst thus obtained are introduced into a tubular quartz glass reactor ($\phi$ 3.2 cm). 132 parts per hour of methanol are vaporized, fed continuously into the reactor and reacted at 420° C. The reaction mixture is condensed. Per hour, 15.4 parts of formaldehyde (selectivity 70% of theory), 0.4 part of water and 84 parts of methanol are obtained.

The Examples which follow indicate the life of the catalysts.

EXAMPLE 6

The catalyst is prepared as described in Example 1 and the reaction is carried out under the same conditions as in Example 1. Samples are taken at intervals, and the content of the reactants in the reaction mixture is determined. The results are shown in Table 1 below. The content of formaldehyde, water and methanol is quoted in g/100 g of reaction mixture and the content of tellurium in mg/kg of reaction mixture.

TABLE 1

| Reaction time (hours) | Content of Formaldehyde | Water | Methanol | Content of tellurium mg/kg | Conversion % | Selectivity % |
|---|---|---|---|---|---|---|
| 8 | 14.8 | 0.8 | 84 | <0.5 | 19.2 | 79.8 |
| 18 | 14.0 | 0.9 | 85 | <0.5 | 20.5 | 77.4 |
| 36 | 13.1 | 0.6 | 86 | <0.5 | 18.2 | 73.0 |
| 72 | 8.4 | 0.6 | 90 | <0.5 | 13.1 | 66.3 |

COMPARATIVE EXAMPLE 7

The catalyst is prepared as described in Comparative Example 3 and the reaction is carried out as described in Example 6. The results are shown in Table 2.

COMPARATIVE EXAMPLE 8

The catalyst is prepared as described in Comparative Example 4 and the reaction is carried out as described in Example 6. The results are shown in Table 3.

The Examples which follow show how the catalysts may be regenerated.

EXAMPLE 9

A catalyst is prepared as described in Example 5 and the reaction is carried out as described in Example 6. After each 8 hours of reaction time, regeneration is effected by passing 200,000 parts by volume of air over the catalyst in the course of one hour, at 550°–600° C. The results are shown in Table 4.

COMPARATIVE EXAMPLE 10

A catalyst is prepared as described in Comparative Example 4 and the reaction is carried out as described in Example 9. The results are shown in Table 5.

TABLE 2

| Reaction time (hours) | Content of Formaldehyde | Water | Methanol | Content of sulfur mg/kg | Conversion % | Selectivity % |
|---|---|---|---|---|---|---|
| 9 | 21.5 | 0.6 | 77 | 170 | 28.3 | 72.4 |
| 18 | 16.3 | 0.5 | 82 | 30 | 24.1 | 65.5 |
| 36 | 12.3 | 1.0 | 86 | 7 | 20.8 | 57.1 |
| 72 | 8.4 | 2.5 | 88 | 3 | 19.7 | 40.2 |

TABLE 3

| Reaction time (hours) | Content of Formaldehyde | Water | Methanol | Content of selenium mg/kg | Conversion % | Selectivity % |
|---|---|---|---|---|---|---|
| 9 | 17.9 | 1.0 | 80 | 830 | 27.3 | 61.9 |
| 18 | 19.4 | 4.5 | 75 | 110 | 27.3 | 68.3 |
| 36 | 21.1 | 0.5 | 78 | 80 | 29.0 | 69.7 |
| 72 | 17.4 | 0.7 | 81 | 80 | 28.2 | 57.1 |

TABLE 4

| Reaction time (hours) | Content of Formaldehyde | Water | Methanol | Content of tellurium mg/kg | Conversion % | Selectivity % |
|---|---|---|---|---|---|---|
| 8 | 13.4 | 0.7 | 85 | <0.5 | 18.9 | 72.6 |
| 16 | 14.4 | 0.8 | 84 | <0.5 | 19.0 | 78.5 |
| 24 | 14.4 | 0.7 | 84 | <0.5 | 19.5 | 75.6 |
| 32 | 14.3 | 0.8 | 84 | <0.5 | 20.3 | 74.7 |
| 40 | 13.4 | 0.9 | 85 | <0.5 | 18.7 | 73.8 |
| 48 | 13.3 | 0.8 | 85 | <0.5 | 18.9 | 74.2 |
| 56 | 14.4 | 0.7 | 84 | <0.5 | 19.8 | 73.9 |
| 64 | 13.9 | 0.9 | 85 | <0.5 | 19.2 | 74.1 |
| 72 | 14.2 | 0.8 | 84 | <0.5 | 19.6 | 73.8 |
| 80 | 14.1 | 0.7 | 84 | <0.5 | 19.5 | 74.2 |

TABLE 5

| Reaction time (hours) | Content of Formaldehyde | Water | Methanol | Content of selenium mg/kg | Conversion % | Selectivity % |
|---|---|---|---|---|---|---|
| 8 | 23.0 | 1.5 | 75 | 130 | 30.6 | 68.0 |
| 16 | 24.0 | 1.3 | 74 | 42 | 34.8 | 65.8 |
| 24 | 21.2 | 1.1 | 77 | 27 | 30.4 | 66.8 |
| 32 | 19.0 | 1.1 | 79 | 6 | 26.0 | 72.6 |
| 40 | 20.6 | 0.9 | 78 | 8 | 28.9 | 69.9 |
| 48 | 18.6 | 1.0 | 80 | 4 | 27.0 | 67.0 |
| 56 | 21.0 | 1.0 | 77 | 7 | 30.5 | 65.6 |
| 64 | 15.8 | 0.9 | 82 | 3 | 24.1 | 64.2 |
| 72 | 15.5 | 0.9 | 82 | 3 | 24.7 | 61.0 |
| 80 | 14.9 | 0.8 | 83 | 3 | 23.4 | 62.0 |

We claim:
1. A process for the preparation of formaldehyde by dehydrogenating methanol in the presence of a catalyst at an elevated temperature, wherein the reaction is carried out in the presence of a catalyst containing copper, zinc and tellurium, at from 300° to 750° C.

2. A process as claimed in claim 1, wherein the reaction is carried out with a catalyst containing 0.01–0.5 atom of zinc and 0.001–0.3 atom of tellurium per atom of copper.

3. A process as claimed in claim 1, wherein the reaction is carried out with a catalyst containing 0.05–0.3 atom of zinc per atom of copper and/or 0.005–0.1 atom of tellurium per atom of copper.

4. A process as claimed in claim 1, wherein the reaction is carried out with a catalyst which, at the end of the reaction, contains 94.2–66.2 percent by weight of the total copper in the form of metallic copper, 4.9–20.5 percent by weight of the total zinc in the form of metallic zinc and 0.9–13.3 percent by weight of the total tellurium in the form of elementary tellurium.

5. A process as clamined in claim 1, wherein the reaction is carried out with a catalyst containing 10–50 gram atoms of copper, 0.5–20 gram atoms of zinc and 0.1–10 gram atoms of tellurium per mole of methanol per hour.

6. A process as claimed in claim 1, wherein the reaction is carried out at from 320° to 600° C.

7. A process as claimed in claim 1, wherein the reaction is carried out with a methanol which is introduced into the catalyst bed in an amount of from 0.5 to 10 kilograms of methanol per hour per liter of catalyst.

* * * * *